(12) United States Patent
Nesterov et al.

(10) Patent No.: US 9,644,072 B2
(45) Date of Patent: May 9, 2017

(54) CONTROLLED RADICAL POLYMERIZATION, AND CATALYSTS USEFUL THEREIN

(75) Inventors: Evgueni E. Nesterov, Baton Rouge, LA (US); Jinwoo Choi, Su-won (KR); Carlos A. Chavez, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 75 days.

(21) Appl. No.: 14/126,514

(22) PCT Filed: Jun. 28, 2012

(86) PCT No.: PCT/US2012/044530
§ 371 (c)(1),
(2), (4) Date: Dec. 16, 2013

(87) PCT Pub. No.: WO2013/006357
PCT Pub. Date: Jan. 10, 2013

(65) Prior Publication Data
US 2014/0114023 A1  Apr. 24, 2014

Related U.S. Application Data

(60) Provisional application No. 61/503,727, filed on Jul. 1, 2011.

(51) Int. Cl.
| | | |
|---|---|---|
| C07C 71/00 | (2006.01) | |
| C08G 75/06 | (2006.01) | |
| B01J 31/24 | (2006.01) | |
| C08F 293/00 | (2006.01) | |
| C07F 15/04 | (2006.01) | |
| C07F 7/18 | (2006.01) | |
| C08G 61/12 | (2006.01) | |
| C08L 65/00 | (2006.01) | |

(52) U.S. Cl.
CPC .......... *C08G 75/06* (2013.01); *B01J 31/2409* (2013.01); *B01J 31/2428* (2013.01); *C07F 7/1856* (2013.01); *C07F 15/045* (2013.01); *C08F 293/005* (2013.01); *C08G 61/126* (2013.01); *C08L 65/00* (2013.01); *B01J 2231/14* (2013.01); *B01J 2531/847* (2013.01); *C08G 2261/126* (2013.01); *C08G 2261/144* (2013.01); *C08G 2261/1412* (2013.01); *C08G 2261/3223* (2013.01); *C08G 2261/417* (2013.01)

(58) Field of Classification Search
None
See application file for complete search history.

(56) References Cited

U.S. PATENT DOCUMENTS

| | | | | |
|---|---|---|---|---|
| 4,709,087 A | * | 11/1987 | Tkatchenko | .......... C07C 263/00 560/339 |
| 7,022,788 B2 | | 4/2006 | Wass | ............................... 26/172 |
| 2009/0043052 A1 | | 2/2009 | McCullough et al. | ........ 525/417 |
| 2010/0084614 A1 | | 4/2010 | Hoffart et al. | ................. 252/500 |
| 2010/0311879 A1 | | 12/2010 | Rieke | ............................ 524/157 |

FOREIGN PATENT DOCUMENTS

WO   WO 97/33198   9/1997

OTHER PUBLICATIONS

Corain et al. Journal of the Chemical Society, Dalton Transaction: Inorganic Chemistry (1972-1999), 4, 283-285, 1975.*
Lee et al. Organometallics, 1985, 4, 539-547.*
Amatore, C. et al., "Rates and Mechanism of Biphenyl Synthesis Catalyzed by Electrogenerated Coordinatively Unsaturated Nickel Complexes," Organometallics, vol. 7, pp. 2203-2214 (1988).
Bronstein, H. A. et al., "Externally Initiated Regioregular P3HT with Controlled Molecular Weight and Narrow Polydispersity," J. Am. Chem. Soc., vol. 131, pp. 12894-12895 (2009).
Carella, A. et al., "Synthesis and application to OPV of highly regioregular polyalkoxyphenylthiophenes catalyzed by copper complexes," Joint Italian-Israeli Workshop on Organic PV, Portici, Italy (Oct. 20, 2011).
Choi, J. et al., Abstract, "Preparation of polythiophene block-copolymers incorporating low energy gap group using nickel catalyzed quasi-living polymerization." 239th ACS National Meeting, San Francisco, CA, 2010. Abstr. Poly-284 (Mar. 21-25, 2010; Abstract published approximately Feb.-Mar. 2010).
Choi, J. et al., Abstract, "Supramolecular organization in stimuli-responsive amphiphilic conjugated polythiophene block copolymers." 66th Southwest and 62nd Southeast ACS Regional Meeting, New Orleans, LA, 2010. Abstr. SESW-1017 (Nov. 30-Dec. 4, 2010; Abstract published approximately Nov. 2010).
Choi, Jinwoo, "Semiconducting Polymers and Block Copolymers Prepared by Chain-Growth Living Polymerization" (PhD Dissertation, Louisiana State University, Baton Rouge, Louisiana, Aug. 2011).
Hwang, E. et al., Abstract, "Nanopatterned surface-immobilized polythiophene thin films by surface initiated metal-catalyzed living polymerization." 66th Southwest and 62nd Southeast ACS Regional Meeting, New Orleans, LA, 2010. Abstr. SESW-478 (Nov. 30-Dec. 4, 2010; Abstract published approximately Nov. 2010).
Hwang, Euiyong, "Surface-Initiated Polymerization as a Novel Strategy towards Preparation of Organic Semiconducting Polymer Thin Films" (PhD Dissertation, Louisiana State University, Baton Rouge, Louisiana May 2011).

(Continued)

*Primary Examiner* — Yun Qian
(74) *Attorney, Agent, or Firm* — John H. Runnels

(57) ABSTRACT

A catalyst is prepared in situ by reaction between an aryl halide and a Ni(0) complex. The catalyst may be used to promote chain-growth polymerization of halogen-substituted Mg or Zn monomers by a controlled radical mechanism. Polymers, co-polymers, block copolymers, polymer thin films, and surface-confined polymer brushes may be produced using the catalyst.

4 Claims, 13 Drawing Sheets

(56) References Cited

OTHER PUBLICATIONS

Iovu, M.C. et al., "Experimental Evidence for the Quasi-'living' Nature of the Grignard Metathesis Method for the Synthesis of Regioregular Poly(3-alkylthiophenes)," Macromolecules, vol. 38, pp. 8649-8656 (2005).

Lanni, Erica L. et al., "Mechanistic Studies on Ni(dppe)Cl$_2$-Catalyzed Chain-Growth Polymerizations: Evidence for Rate-Determining Reductive Elimination," J. Am. Chem. Soc., vol. 131, pp. 16573-16579 (2009).

Lusker, K. L. et al., Abstract, "Nanopatterns as selective sites for surface chemical reactions." 66th Southwest and 62nd Southeast ACS Regional Meeting, New Orleans, LA, 2010. Abstr. SESW-375 (Nov. 30-Dec. 4, 2010; Abstract published approximately Nov. 2010).

Marshall, N. et al., "Surface-initiated polymerization of conjugated polymers," Chem. Commun., vol. 47, pp. 5681-5689 (2011).

Mauer, R. et al., "The Impact of Polymer Regioregularity on Charge Transport and Efficiency of P3HT:PCBM Photovoltaic Devices," Adv. Funct. Mater., vol. 20, pp. 2085-2092 (2010).

Miyakoshi, R. et al., "Catalyst-Transfer Polycondensation. Mechanism of Ni-Catalyzed Chain-Growth Polymerization Leading to Well-Defined Poly(3-hexylthiophene)," J. Am. Chem. Soc., vol. 127, pp. 17542-17547 (2005).

Nesterov, E. et al., Abstract, "Nanopatterned polythiophene thin films prepared by surface-initiated polymerization." International Chemical Congress of Pacific Basin Societies (Pacifichem 2010), Honolulu, HI, 2010. Abstr. 33 (Dec. 15-20, 2010; Abstract published Jul. 12, 2010).

Nesterov, E. et al., Abstract, "Highly efficient externally initiated Kumada polycondensation: controlled preparation of complex polythiophene architectures." International Chemical Congress of Pacific Basin Societies (Pacifichem 2010), Honolulu, HI, 2010. Abstr. 1192 (Dec. 15-20, 2010; Abstract published Jul. 12, 2010).

Senkovskyy, V. et al., "Conductive Polymer Brushes of Regioregular Head-to-Tail Poly(3-alkylthiophenes) via Catalyst-Transfer Surface-Initiated Polycondensation," J. Am. Chem. Soc., vol. 129, pp. 6626-6632 (2007).

Tkachov, R. et al., "Random Catalyst Walking along Polymerized Poly(3-hexylthiophene) Chains in Kumada Catalyst Transfer Polycondensation," J. Am. Chem. Soc., vol. 132, pp. 7803-7810 (2010).

Yokozawa, T. et al., "Chain-Growth Condensation Polymerization for the Synthesis of Well-Defined Condensation Polymers and π-Conjugated Polymers," Chem. Rev., vol. 109, pp. 5595-5619 (2009).

Sheina, Elena E. et al., "Chain Growth Mechanism for Regioregular Nickel-Initiated Cross-Coupling Polymerizations," Macromolecules, vol. 37, pp. 3526-3528 (2004).

\* cited by examiner

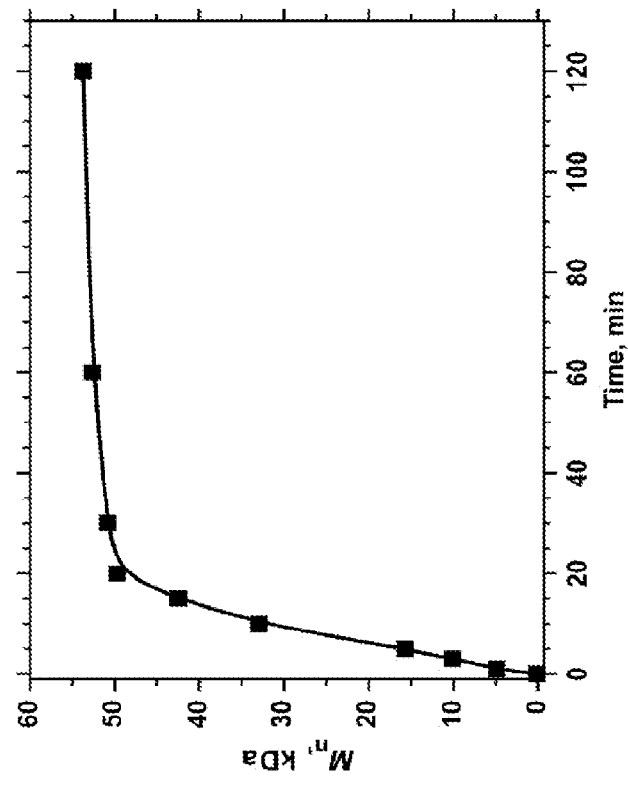
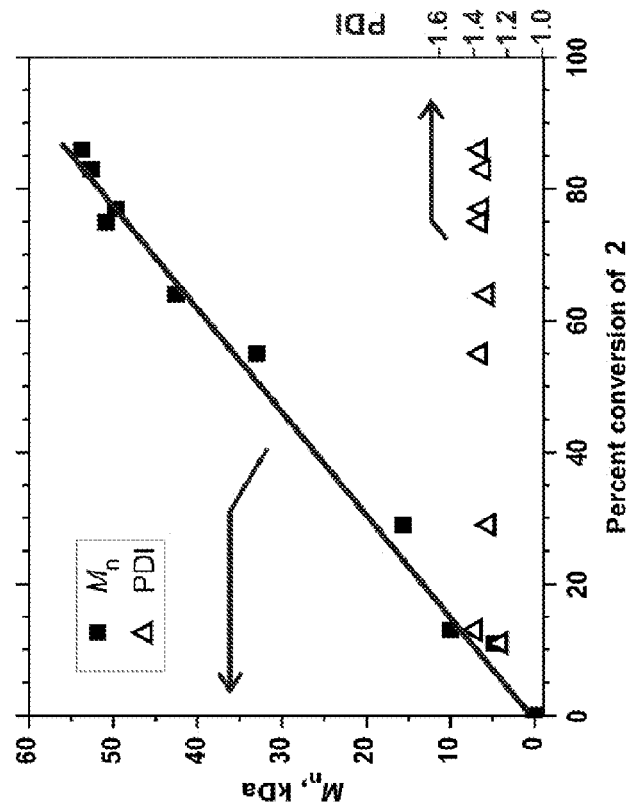
Fig. 2A
Fig. 2B

NIL$_2$ = Ni(0) complex with two bidentate diphosphine ligands
R = variously substituted aromatic or aliphatic groups at various positions, or H
X = Cl, Br, I
Y = functional group for chemical attachment to the surface
(e.g. Silyl, Phosphonate, Carboxylate, etc.

Ar, Ar', and Ar" = any monoaromatic and oligoaromatic disubstituted units, for example (but not limited to):

or $C_1$ to $C_{12}$ substituted homologs

CONTROLLED RADICAL POLYMERIZATION, AND CATALYSTS USEFUL THEREIN

This is the U.S. national stage of international application PCT/US2012/044530, international filing date Jun. 28, 2012, which claims the benefit of the Jul. 1, 2011 filing date of U.S. provisional patent application Ser. No. 61/503,727 under 35 U.S.C. §119(e). The complete disclosure of the 61/503,727 priority application is hereby incorporated by reference in its entirety.

This invention was made with support from the United States Government under grants CHE-0547895 and DMR-1006336 awarded by the National Science Foundation. The United States Government has certain rights in this invention.

TECHNICAL FIELD

Conjugated polymers, particularly polythiophenes (PTs) are widely used in electronics and optoelectronics (e.g., thin-film transistors, photovoltaic cells, polymeric light-emitting diodes), as well as in chemosensing and biosensing devices. There is an unfilled need for new PTs, polythiophene copolymers, and other conjugated polymers having properties that can be fine-tuned to meet the requirements of particular applications; for improved methods of synthesizing PTs and their copolymers; and for improved catalysts suitable for catalyzing such syntheses and in catalyzing related reactions.

BACKGROUND ART

"Living polymerization" is a form of addition polymerization in which chain termination reactions are absent or are strongly inhibited. Polymer chains typically grow at a more constant rate in living polymerization than is seen in other types of polymerization, and the resulting chain lengths tend to be similar (i.e., the polymers have a very low polydispersity index). Living polymerization is useful for synthesizing block copolymers. A block copolymer can be synthesized in two or more stages, with each stage containing a different monomer.

One method that has been used for preparing PTs and their block copolymers is living polymerization based on the Ni-catalyzed Kumada polymerization of 5-bromo-2-thienylmagnesium monomers. Mechanistic studies have suggested that this polymerization proceeds through a cyclic catalysis mechanism involving a series of oxidative addition/reductive elimination steps. To take full advantage of the "living" polymerization mechanism, the reaction is typically conducted at ambient temperature. The reaction generally yields polymers having low to medium molecular weights due to the low reactivity of the Ni(II) catalysts that have been used, such as Ni(dppp)Cl$_2$ (where dppp is 1,3-bis(diphenylphosphino)propane). The Ni center typically has a square-planar geometry. However, in this system it is possible for the propagating Ni(II) reactive center to transfer from one chain to another during polymerization, so this polymerization might more accurately be described as "quasi-living." True "living" polymerization would be enhanced by the availability of highly reactive universal catalytic systems.

Prior approaches to preparing regioregular, high molecular weight poly(3-alkylthiophene)s have required relatively high temperatures and long reaction times. As a consequence, the resulting polymers have shown decreased regioregularity (85-95%), and despite high reaction temperatures and long reaction times, have still shown relatively low molecular weights. The difficulty in obtaining high-regioregularity (around 100%) polythiophenes in substantial amounts hinders development of practical applications of these materials and has prompted some studies of less-regioregular polythiophenes as possible substitutes.

V. Senkovskyy et al., *J. Am. Chem. Soc.* 2007, 129, 6626-6632; R. Tkachov et al., *J. Am. Chem. Soc.* 2010, 132, 7803-7810; and H. Bronstein et al., *J. Am. Chem. Soc.* 2009, 131, 12894-12895 reported an externally initiated living polymerization process in which a stable aryl-Ni(II) initiating complex, e.g. σ-complex 1 (FIG. 1A), was used to catalyze the polymerization of Grignard monomer 2. The catalytic initiator was stabilized by a bidentate phosphine ligand. The initiator was prepared by ligand exchange between the initial complex with monodentate phosphine ligands which, in turn, may be prepared by oxidative addition of an aryl halide to Ni(PPh$_3$)$_4$ (FIG. 1A). This external initiation route enhances the utility of living catalyst-transfer polymerization. For example, it makes it possible to grow surface-immobilized PT brushes. However, the previously-reported process requires a relatively complicated preparation to make the catalytic initiator; and it is possible for the initiator to be contaminated with monodentate PPh$_3$ ligand. Any such contamination can decrease catalytic activity, and limits practical applications of this method.

C. Amatore et al., *Organometallics* 1988, 7, 2203-2214 reported that Ni(0) complexes containing bidentate phosphine ligands do not react with aryl halides.

T. Yokozawa et al., *Chem. Rev.* 2009, 109, 5595-5619 provides a review summarizing recent research in chain-growth condensation polymerization.

N. Marshall et al., *Chem. Commun.*, 2011, 47, 5681-5689 provides a review summarizing recent research in surface-initiated polymerization of conjugated polymers.

M. Iovu et al., *Macromolecules* 2005, 38, 8649-8656 reported a Grignard metathesis polymerization of 3-alkylthiophenes by a quasi-living chain growth mechanism using a 1,3-bis(diphenylphosphino)propane]dichloronickel(II) (Ni(dppp)Cl$_2$) initiator. The authors reported that the reaction proceeded through a cycle of oxidative addition/reductive elimination steps.

R. Miyakoshi et al., *J. Am. Chem. Soc.* 2005, 127, 17542-17547 hypothesized that the mechanism for chain-growth polymerization of 2-bromo-5-chloromagnesio-3-hexylthiophene with Ni(dppp)Cl$_2$ involved a coupling reaction between a Grignard thiophene and the growing polymer via the Ni catalyst, which was transferred intramolecularly to the terminal C—Br bond of the elongated molecule, a mechanism that the authors called a catalyst-transfer polycondensation. That is, the polycondensation was said to proceed with the catalyst transferring to and activating the elongated polymer end group.

E. Lanni et al., *J. Am. Chem. Soc.* 2009, 131, 16573-16579 proposed mechanisms for the Ni(dppe)Cl$_2$-catalyzed chain-growth polymerization of 4-bromo-2,5-bis(hexyloxy)phenylmagnesium chloride and 5-bromo-4-hexylthiophen-2-ylmagnesium chloride. Both polymerizations exhibited first-order dependence on the catalyst concentration, but were nearly independent of the monomer concentration. $^{31}$P NMR spectroscopic studies suggested that the resting states were unsymmetrical Ni$^{II}$-biaryl and Ni$^{II}$-bithiophene complexes. In combination, the data suggested reductive elimination was the rate-determining step for both monomers, followed by subsequent intracomplex oxidative addition, leading to chain growth.

V. Senkovskyy et al., *J. Am. Chem. Soc.* 2007, 129, 6626-6632 described a method to grow conductive polymer brushes of regioregular head-to-tail poly(3-alkylthiophenes) via surface-initiated, catalyst-transfer chain growth polycondensation of 2-bromo-5-chloromagnesio-3-alkylthiophene. The method used a Ni(II) macroinitiator formed by reaction of Ni(PPh$_3$)$_4$ with photo-crosslinked poly-4-bromostyrene films. Exposing the initiator layers to the monomer solution led to selective chain growth polycondensation of the monomer onto the surface, thereby producing conductive polymer brushes. The brushes were said to be mechanically robust, and to be stable against delamination.

H. Bronstein et al., *J. Am. Chem. Soc.* 2009, 131, 12894-12895 reported the polymerization of a thiophene Grignard reagent, initiated from an externally added cis-chloroaryl (dppp) nickel complex, to produce a regioregular poly(3-hexylthiophene) with controlled molecular weights and narrow polydispersities.

Regioregularity has often been considered to be an important factor in optimizing the electronic properties of polythiophenes. See, e.g., A. Carella et al., "Synthesis and application to OPV of highly regioregular polyalkoxyphenylthiophenes catalyzed by copper complexes," Joint Italian-Israeli Workshop on Organic PV, Portici, Italy, Oct. 20, 2011. However, there have also been reports that the regioregularity of the polymer may not have a significant effect on the power conversion efficiency of a photovoltaic device. See, e.g., R. Mauer et al., *Adv. Funct. Mater.* 2010, 20, 2085-2092.

DISCLOSURE OF THE INVENTION

We have discovered a novel catalyst useful in controlled radical polymerization, for example Compound 4, and an efficient method for preparing the novel catalysts by the direct oxidative addition of an aryl halide to a nickel(0)-containing species such as Ni(dppp)$_2$ (E.g., FIG. 1B). The catalyst facilitates the controlled radical polymerization of 5-bromo-2-thienylmagnesium monomers, as well as the controlled radical polymerization of other halogen-substituted Grignard reagent monomers or of halogen-substituted organozinc monomers. The polymerization is highly efficient. The novel catalyst allows the controlled preparation of regioregular polythiophenes and block copolymers, as well as other conjugated polymers such as poly(p-phenylene)s, polyfluorenes, etc. It may be used not only to prepare conjugated polymers in solution, but also to prepare surface-confined films of conjugated polymers. The novel catalytic initiators are convenient to synthesize, and provide a powerful means to prepare, in highly controlled fashion, polythiophenes and other conjugated polymers with high regioregularity and high molecular weights. Polymerization carried out with the novel catalyst is truly living, with no reactive end transfer.

The novel catalyst contains a Ni(I) center, in marked contrast to earlier catalysts based on a Ni(II) center. Previously reported thiophene catalysts have primarily proceeded through a series of oxidative addition/reductive elimination steps. By contrast, the novel catalyst proceeds through an unconventional radical living chain-growth polymerization mechanism. In view of what other workers have suggested, it was surprising that aryl halides would even react with Ni(dppp)$_2$, as we used to make the novel catalyst.

Surprisingly, contrary to the report by Amatore et al. (1988) that Ni(0) complexes containing bidentate phosphine ligands do not react with aryl halides, we found that such reactions can indeed occur. The first such reaction we investigated was the reaction between 2-bromobithiophene (Compound 3) and Ni(dppp)$_2$. We found that the reaction led to the formation of the Ni(I) derivative 4. Compound 4 may be used as a highly efficient catalytic initiator of controlled radical polymerization of Grignard monomers such as compound 2, or of other organometallic monomers such as organozinc monomers.

The novel catalyst is stable. Unlike some prior catalysts, it does not need to be prepared in situ. Instead, the catalyst may be prepared in solution and stored in solution under refrigeration for weeks or months, to be used when needed.

The novel catalytic process gives 95% or greater regioregularity for some polymerizations. Indeed, within resolving ability, essentially 100% regioregularity has been achieved for at least some polymers, for example essentially 100% regioregular poly(3-alkylthiophene)s. Regioregularity gives rise to better electronic properties.

The concept of "regioregular" polythiophenes may be illustrated as follows:

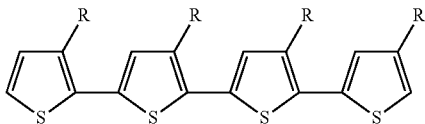

The above structure is a regioregular polymer. There is regular "R" group placement at the 3-positions of the thiophene rings, which tends to enhance electronic properties.

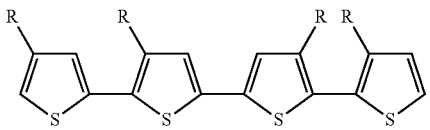

The above structure is not a regioregular polymer. Irregular placement of the "R" groups, i.e. at random 3- and 4-positions on the thiophene rings, tends to diminish useful electronic properties such as electrical conductivity.

The novel catalyst sustains polymerization to unprecedentedly high molecular weights. The limit of polymerization appears to be imposed solely by the polymer's solubility. Higher molecular weight also tends to improves electronic properties.

The product's molecular weight can be controlled by changing the amount of catalyst, e.g. catalyst 4, used in the polymerization. The distribution of molecular weights (the polydispersity) is typically narrow (less than 1.5), reflecting the living chain-growth character of the novel radical polymerization. The linear dependence of the molecular weight of polythiophene made from monomer 2 (FIG. 2A) is evidence of the living chain-growth mechanism of polymerization.

Block co-polymers are readily synthesized with the novel catalysts.

The catalyst can be made inexpensively. It can be used in both homogeneous and heterogeneous reactions.

The catalytic initiators may be prepared by reaction of easily available aryl halides (Ar—X, where Ar=substituted or unsubstituted thienyl, or substituted or unsubstituted phenyl; X=F, Cl, Br, I).

Exemplary embodiments of the invention include the following:

A composition of matter comprising

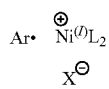

wherein:
Ar. denotes a substituted or unsubstituted aryl radical;
$L_2$ denotes two bidentate ligands, wherein the two bidentate ligands may be the same or different; and
$X^-$ denotes a monovalent anion.

A composition as described, wherein said composition is in solution.

A composition as described, wherein:
Ar. denotes a substituted or unsubstituted, fused or unfused benzene, thiophene, pyrrole, or furan radical;
$L_2$ denotes two substituted or unsubstituted diphosphines, wherein the two substituted or unsubstituted diphosphines may be the same or different; and
$X^-$ denotes a monovalent halide.

A composition as described, wherein:
Ar. denotes the bithiophen-2-yl radical;
each $L_2$ denotes 1,3-bis(diphenylphosphino)propane; and
$X^-$ denotes bromide.

A composition as described, wherein said composition is covalently bound to a surface via a linker moiety.

A composition as described, wherein said linker comprises silyl, phosphonate, carboxylate, or $(CH_2)_n$.

A method of synthesizing a catalyst, said method comprising reacting in solution Ar—X with $NiL_2$ wherein:
Ar denotes substituted or unsubstituted aryl;
$L_2$ denotes two bidentate ligands, wherein the two bidentate ligands may be the same or different; and
X denotes a halogen.

A method as described, wherein:
Ar denotes a substituted or unsubstituted, fused or unfused benzene, thiophene, pyrrole, or furan radical; and
$L_2$ denotes two substituted or unsubstituted diphosphines, wherein the two substituted or unsubstituted diphosphines may be the same or different.

A method as described, wherein:
Ar denotes bithiophen-2-yl;
each $L_2$ denotes 1,3-bis(diphenylphosphino)propane; and
X denotes bromine.

The catalyst produced by one of the methods described.

A process for synthesizing a polymer, said process comprising polymerizing a first monomer X'—Ar'-MX" in the presence of a composition or catalyst as described, wherein:
X' denotes a monovalent halide
Ar' denotes substituted or unsubstituted aryl;
M denotes Mg or Zn; and
X" denotes a monovalent halide.

A process for synthesizing a block copolymer, said process comprising continuing the polymerization process as described after a time with a second monomer X'—Ar"-MX" wherein
Ar" denotes substituted or unsubstituted aryl, wherein Ar" is different from Ar'; and
X', M, and X" are as previously defined; wherein each of X', M, and X", respectively, may be the same or different in the first and second monomers.

A process for synthesizing a polymer, said process comprising polymerizing a first monomer X'—Ar'-MX" in the presence of a composition or catalyst as described, wherein:
X' denotes a monovalent halide
Ar' denotes substituted or unsubstituted aryl;
M denotes Mg or Zn; and
X" denotes a monovalent halide.

A process for synthesizing a block copolymer, said process comprising continuing the polymerization process as described after a time with a second monomer X'—Ar"-MX" wherein
Ar" denotes substituted or unsubstituted aryl, wherein Ar" is different from Ar'; and
X', M, and X" are as previously defined; wherein each of X', M, and X", respectively, may be the same or different in the first and second monomers.

BRIEF DESCRIPTION OF THE DRAWINGS

FIG. 2 (A) depicts the number average molecular weight ($M_n$) and the polydispersity index (PDI) of polythiophene P1 as a function of the percentage conversion of monomer 2 (solid line=calculated data). FIG. 2(B) depicts the $M_n$ of polymer P1 as a function of polymerization time.

MODES FOR CARRYING OUT THE INVENTION

General Procedures

Figure 1A:
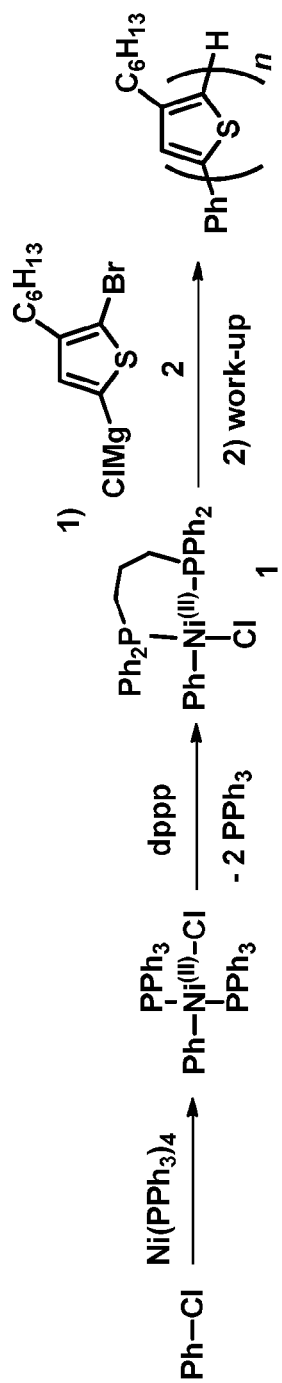
FIG. 1(A) depicts the preparation of Ni(II) square-planar catalytic initiator 1 according to the method of Senkovskyy et al. (2007) and Bronstein et al. (2009).

FIG. 1 depicts: (A) the preparation of a Ni(II) catalytic initiator 1 according to the method of Senkovskyy et al. (2007) and Bronstein et al. (2009); and (B) the preparation of the novel Ni(I) radical catalytic initiator 4 by the novel method described here.

Example 1

All reactions were performed under an atmosphere of dry nitrogen (unless mentioned otherwise). Melting points were determined in open capillaries and are uncorrected. Column chromatography was performed on silica gel (Sorbent Technologies, 60 Å, 40-63 μm) slurry packed into glass columns. Tetrahydrofuran (THF), ether, toluene, hexanes, and dichloromethane were dried by passing through activated alumina;

and N,N-dimethylformamide (DMF) by passing through activated molecular sieves; using a PS-400 Solvent Purification System from Innovative Technology, Inc. The water content of the solvents was periodically controlled by Karl Fischer titration (using a DL32 coulometric titrator from Mettler Toledo). Isopropylmagnesium chloride (2.0 M solution in THF) was purchased from Acros Organics. All other reagents and solvents were obtained from Aldrich or from Alfa Aesar, and were used without further purification. $^1$H NMR spectra were recorded at 250 and 400 MHz and are reported in ppm downfield from tetramethylsilane; $^{31}$P NMR spectra were obtained at 161 MHz and are reported in ppm relative to 80% aqueous $H_3PO_4$ as an external standard. UV-visible spectra were recorded on a Varian Cary 50 UV-Vis spectrophotometer. GPC analysis of polymers was performed with Agilent 1100 chromatograph equipped with two PLgel 5 μm MIXED-C and one PLgel 5 μm 1000 Å columns connected in series, using THF as a mobile phase, and calibrated against polystyrene standards. High resolution mass spectra were obtained at the LSU Department of Chemistry Mass Spectrometry Facility using the MALDI-TOF method with a terthiophene matrix. Atomic force microscopy images were acquired with an Agilent 5500 (PicoPlus) system with PicoScan v. 5.3.3 software.

Example 2

The Ni(dppp)$_2$ reagent used in these reactions can be prepared, for example, by the method of B. Corain el al., *J. Organomet. Chem.* 1971, 28, 133-136. Briefly, to a vigorously stirred mixture of 1.50 g (5.84 mmol) of nickel(II) bis(acetylacetonate) (Ni(acac)$_2$) and 4.82 g (11.7 mmol) of 1,3-bis(diphenylphosphino)propane (dppp) in 80 ml of ether and 15 ml of toluene, a solution of i-Bu$_3$Al (19.8 ml of 1.0 M solution in hexanes, 19.8 mmol) was added slowly over a 1 h period (by syringe pump) under Ar atmosphere. The resulting mixture was stirred at room temperature for 24 h. During this period the solution's color changed from bright green to bright red. The reaction mixture was left unperturbed for an additional 24 h, and the resulting precipitate was filtered under argon, and washed with excess ether to give 3.5 g (68%) of the product as a bright-orange solid material, mp 281° C., decomp. (lit. mp 281-283° C.).

Example 3

Figure 1B:
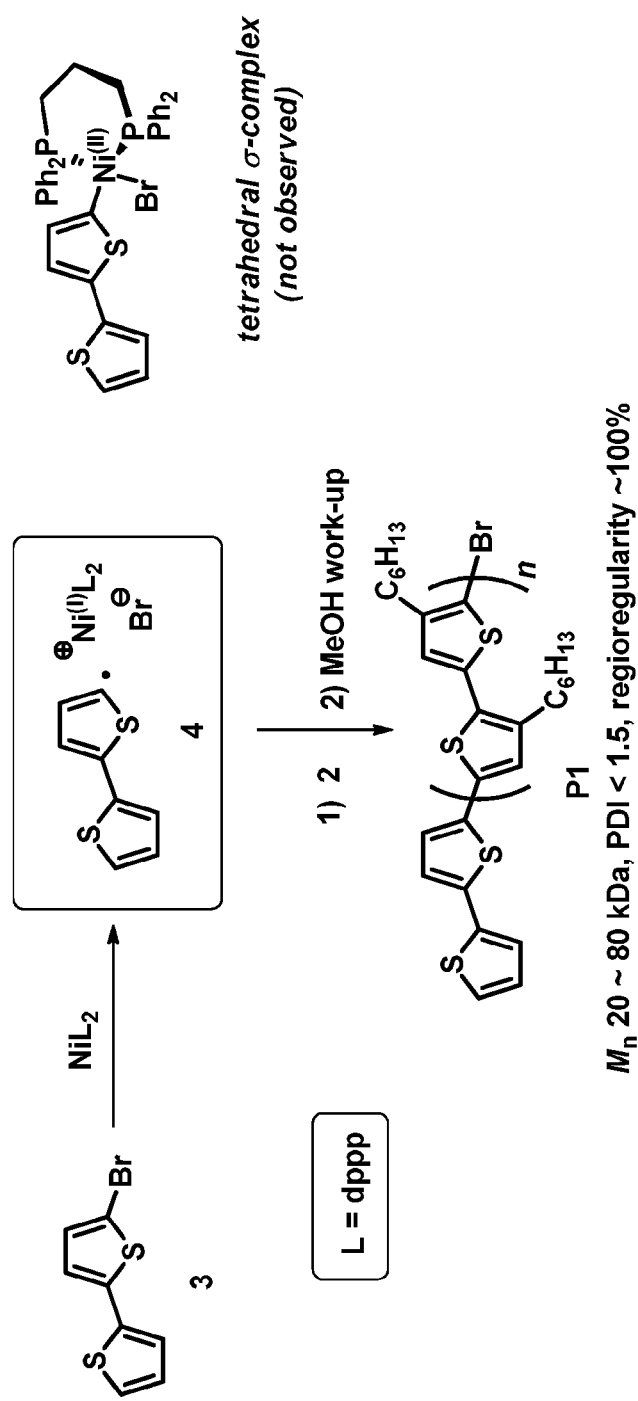
FIG. 1(B) depicts the preparation of the novel Ni(I) radical catalytic initiator 4 by the novel method described here.

An equimolar mixture of Compound 3 and Ni(dppp)$_2$ was stirred in toluene at 40° C. The reaction was monitored by $^{31}$P NMR, which allows Ni(dppp)$_2$ to be identified easily by its characteristic singlet at 12.8 ppm. We were disappointed that initially we did not observe any significant new signals; those initial results seemed to indicate that no reaction was occurring, consistent with reports in the earlier literature. We nevertheless allowed the reaction to continue running for longer times, and we noticed that the intensity of the 12.8 ppm singlet gradually decreased, almost disappearing after 72 hours. If the decreasing 12.8 ppm signal had resulted simply from thermal degradation of Ni(dppp)$_2$, then we should have observed new $^{31}$P NMR signals corresponding to the degradation products, but no such new signals were seen. These observations led us to conclude that Compound 3 and Ni(dppp)$_2$ had reacted with one another to produce a stable paramagnetic product that would not be detected by $^{31}$P NMR. There are two such paramagnetic species that might be possible, both of which are depicted in FIG. 1B: a tetrahedral Ni(II) σ-complex, and a ligand-stabilized radical Ni(I) complex 4. Our experimental observations (described below) support the latter, the ligand-stabilized radical Ni(I) complex 4.

Example 4

Radical species are common intermediates in the oxidative polymerization of thiophene monomers, e.g. thiophene polymerization via Fe(III) salts as stoichiometric oxidants or via electrochemical oxidation. However, to the inventors' knowledge radical species have not previously been reported as intermediates in a metal-catalyzed polymerization of thiophenes and other aromatic monomers. Because the radicals involved in oxidative polymerization are high-energy species, stoichiometric oxidative polymerizations typically have low regioselectivity. E.g., both the Fe(III)-promoted and the electrochemical polymerizations are characterized by low regioselectivity. Most surprisingly, we obtained completely regioregular poly(3-alkylthiophene)s (nearly 100% regioregularity) with the novel process, even though our evidence suggests that the process proceeds through a radical mechanism. For example, we obtained nearly 100% regioregularity by adding a catalytic amount of an in situ-prepared toluene solution of complex 4 to a solution of Grignard monomer 2 in THF, and allowing the reaction to proceed for 1 hour at 35° C., followed by precipitation of the reaction mixture into methanol. The poly(3-hexylthiophene) (P3HT) compound P1 (FIG. 1B) product was completely regioregular. Regioregularity, defined as the fraction of head-to-tail (HT) coupled 3-hexylthienyl units, was close to 100% as determined by $^1$H NMR. The molecular weight of Compound P1 was strongly dependent on the molar percentage of Complex 4 in the polymerization mixture, consistent with a living chain-growth mechanism.

Example 5

FIG. 2 (A) depicts the number average molecular weight ($M_n$) and the polydispersity index (PDI) of polymer P1 as a function of the percentage conversion of monomer 2 (solid line=calculated data). FIG. 2(B) depicts the $M_n$ of polymer P1 as a function of polymerization time. Polymerization was carried out with 0.25 mol % of Complex 4. $M_n$ and PDI ($M_w/M_n$) were determined by gel permeation chromatography relative to polystyrene standards, and percent conversion of monomer 2 was determined by $^1$H NMR.

Example 6

Once a solution of Complex 4 had been prepared, it could be stored for at least a few weeks in a freezer without losing its catalytic activity. (We do not have data for longer storage times.) However, we have not been able to isolate Complex 4 as a solid state composition that retains catalytic activity. Since paramagnetic Complex 4 was NMR-silent, there was no easy way to quantify the amount of Complex 4 that was produced in situ from the reaction of Compound 3 and Ni(dppp)$_2$. We observed that if Compound 3 and Ni(dppp)$_2$ were allowed to react for at least 72 hours (a time that corresponded to almost complete disappearance of the Ni(dppp)$_2$ signal from the $^{31}$P NMR spectrum), then the molecular weight of Compound P1 could be accurately predicted based on the initial amount of the Ni(dppp)$_2$, an observation that was consistent with the essentially complete conversion of Ni(dppp)$_2$ to Complex 4. In some instances we found it more convenient to allow Compound 3 and Ni(dppp)$_2$ to react for 24 hours, and in such a case the conversion to Complex 4 occurred with a yield around 60%, as determined by the molecular weight of the polymer P1 produced with the resulting catalytic solution.

Example 7

In multiple experiments, we have consistently prepared P3HT Compound P1 with a number average molecular weight ($M_n$) ranging between 20 kDa and 80 kDa, depending on the molar fraction of catalytic Complex 4. Higher molecular weights were not produced under the particular reaction conditions we employed, likely due to the limited solubility of P3HT having a molecular weight above 80 kDa. In all cases, the P3HT polymers produced via Complex 4 had high regioregularity (close to 100%), and a narrow polydispersity index (PDI≤1.5). The number average molecular weight $M_n$ of Polymer P1 was linearly dependent on the conversion of Grignard monomer 2 (FIG. 2A), an observation that is consistent with a living chain growth mechanism of polymerization.

Polymerization was rapid and efficient. Polymerization was practically complete 20 minutes after the addition of Complex 4 to Grignard monomer 2 (FIG. 2B). The propagating reacting center likely had significant radical character, as we could not detect any $^{31}P$ NMR signals during polymerization. (For this experiment, polymerization was carried out in an NMR tube containing 5 mol % of Complex 4 in order to obtain a good NMR signal). However, quenching the reaction mixture with methanol immediately produced a broad $^{31}P$ NMR signal at −20 ppm, corresponding to the free dppp ligand.

Example 8

Supporting our proposed radical polymerization mechanism was our observation that using the activator Ni(dppp)$_2$ alone did not result in polymerization of monomer 2—only a very low (<5%) yield of P3HT was obtained, even following an extended reaction time. (We hypothesize that even in this case the polymerization was likely catalyzed not by Ni(dppp)$_2$ itself, but instead by a catalytic initiator analogous to Complex 4, formed by reaction between Ni(dppp)$_2$ and some residual, unreacted 2,5-dibromo-3-hexylthiophene that had been used to prepare Grignard monomer 2.) When Complex 4 was used as the catalytic initiator, the presence of a bithiophene terminus in polymer P1 was unambiguously confirmed by MALDI-TOF end-group analysis. These observations strongly supported our hypothesis that Complex 4 was the initiating catalytic species for polymerization.

Example 9

A major difference between the mechanism of polymerization as initiated by Complex 4 and that for conventional catalyst-transfer Kumada polymerization of Compound 2, as catalyzed by Ni(dppp)Cl$_2$, was demonstrated by adding to the reaction mixture TEMPO (2,2,6,6-tetramethylpiperidine-1-oxyl), which is a stable radical inhibitor. When polymerization of Grignard monomer 2 was catalyzed by Ni(dppp)Cl$_2$ (0.3 mol %) in the presence of 1 mol % TEMPO, the reaction was unaffected by the presence of the radical inhibitor. By contrast, adding the same amount of TEMPO to a reaction mixture containing 0.3 mol % of Compound 4 completely inhibited polymerization, and no polymer was produced. The inhibition by TEMPO strongly supported the conclusion that polymerization catalyzed by Complex 4 proceeds through radical intermediates.

Example 10

Figure 3A:
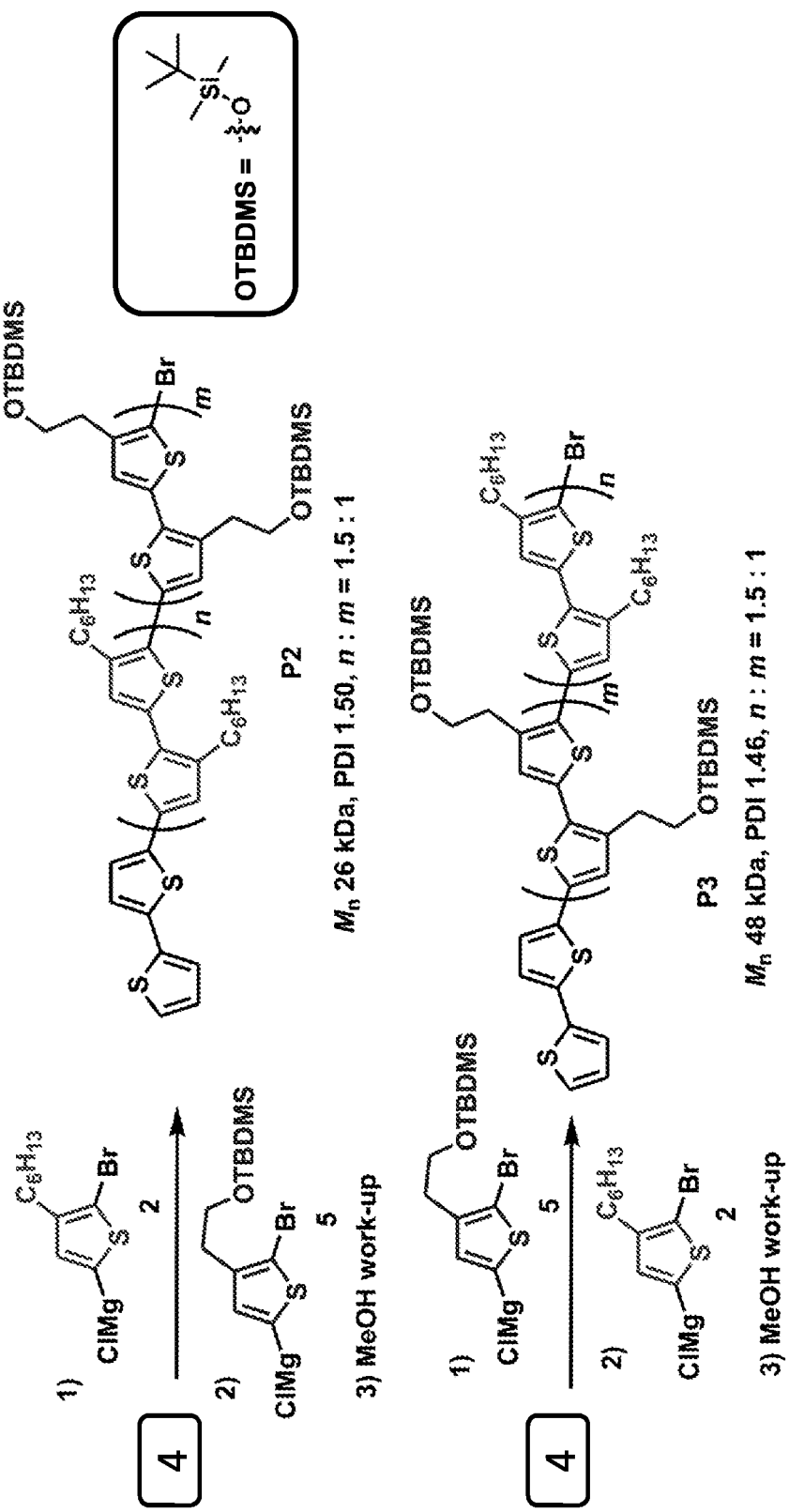
FIG. 3(A) depicts the preparation of block copolymers P2 and P3.
Figure 3B:
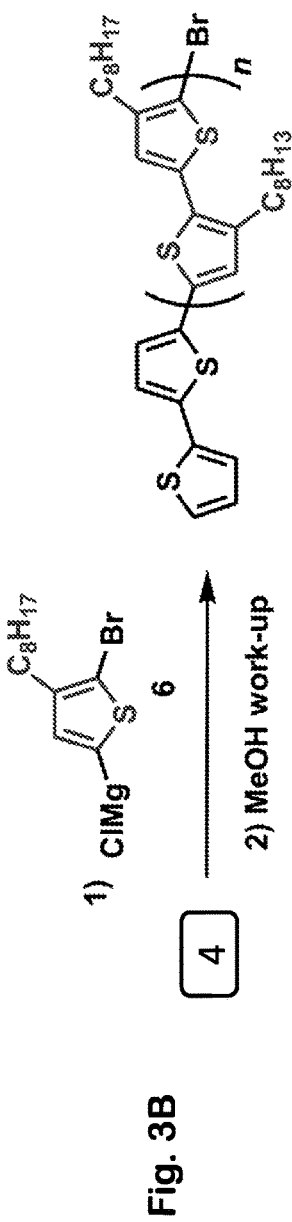
FIG. 3(B) depicts the preparation of polymer P4 and the end-group composition as determined from MALDI-TOF data.
Figure 3C:
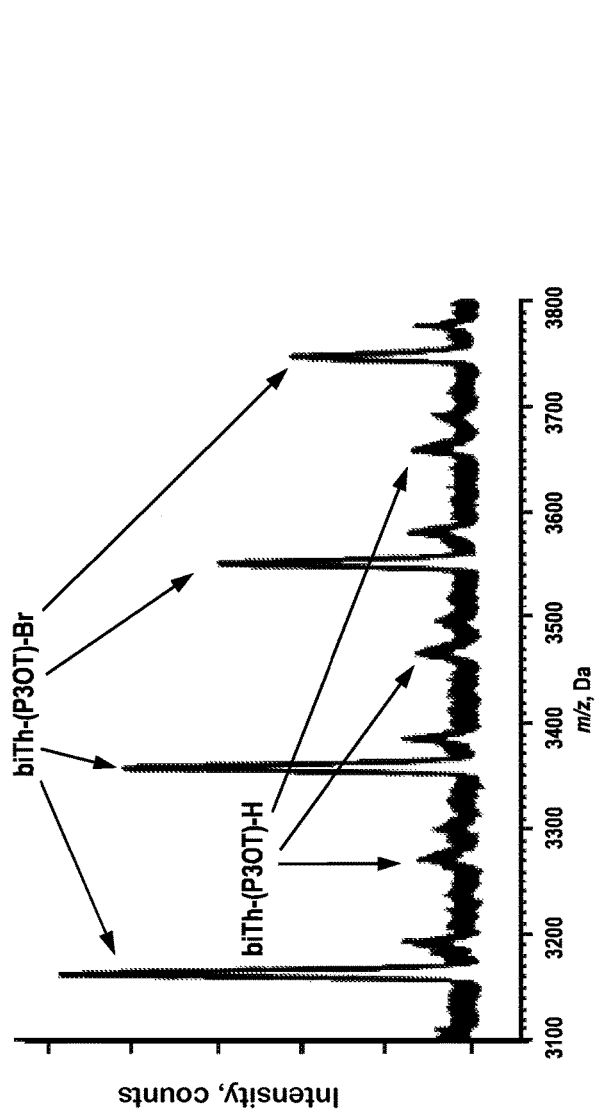
FIG. 3(C) depicts a portion of the MALDI-TOF spectrum for polymer P4, along with several peak assignments, to illustrate how the end-group composition was determined.

FIG. 3(A) depicts the preparation of block copolymers P2 and P3 by living radical polymerization. FIG. 3(B) depicts the preparation of polymer P4 and its end-group composition as determined by MALDI-TOF data. FIG. 3(C) depicts a portion of the MALDI-TOF spectrum for polymer P4, along with several peak assignments.

Example 11

With a true "living" polymerization, block copolymers can be conveniently produced by sequentially adding different monomers to the reaction mixture, and allowing sufficient time in between for complete reaction. For example, by adding Grignard monomers 2 and 5 to a solution of the external catalytic initiator 4 (1 mol %) at 35° C., we prepared two completely regioregular block copolymers P2 and P3 (~100% HT coupling within each block). Copolymers P2 and P3 each had high molecular weights, and both could be prepared with relatively short polymerization times. See FIG. 3(A).

Example 12

The composition of a polymer chain's end groups (e.g., as determined by MALDI-TOF analysis) can reveal details about the mechanism of its polymerization. However, due to the similarity in molecular weights of the bithien-2-yl (biTh) end group (165 Da) and the 3-hexylthien-2,5-diyl polymer repeating unit (166 Da), MALDI-TOF did not permit unambiguous confirmation that the bithiophene terminal unit from catalytic initiator 4 had been incorporated into the P1 chain. To help resolve this ambiguity, we prepared a new polymer P4, poly(3-octylthiophene) (P3OT), by polymerizing Grignard monomer 6 in the presence of 0.3 mol % of catalytic initiator 4. See FIG. 3(B). Polymer P4 ($M_n$ 57 kDa, PDI 1.5) was completely regioregular (essentially 100%). Because the molecular weight of the 3-octylthien-2,5-diyl repeating unit (194 Da) was substantially different from the molecular weight of the biTh unit, we were able to confirm that the bithiophene terminal unit had been incorporated into polymer P4. Mass spectrometry also confirmed that the terminal group at the other end of the polymer chain was predominantly Br (i.e., P4 comprised mainly biTh-(P3OT)-Br chains). The predominance of the Br terminal group contrasted with the H-termination that would typically be observed in catalyst-transfer polymerization using a traditional Ni(II) catalyst. A terminal Br would be expected if the Br anion remained closely associated with the propagating radical center. In the absence of monomer a less reactive, "dormant" radical state would be observed (or perhaps the reversible transfer of a bromine atom back to a thienyl carbon).

Example 13

The mechanism we have proposed shares some analogies with the mechanism for classical Atom Transfer Radical Polymerization (ATRP) of activated alkenes, in which a ligand-stabilized reactive metal center remains dormant in the absence of monomer with which to react. A characteristic of the ATRP mechanism is that the halogen atom from the initiating species remains closely associated with the propagating polymerization center, and eventually becomes a terminal halogen atom in the polymer product. To help confirm the proposed mechanism we wished to confirm whether the initial bromine atom from catalytic initiator 4 was indeed transferred throughout the entire sequence of chain growth steps to become a terminal atom in the resulting PT polymer. To trace the fate of the initial bromine atom, we polymerized 5-iodo-3-octyl-2-thienylmagnesium chloride, Grignard monomer 7, which contains an iodine atom and which was prepared from 2,5-diiodo-3-octylthiophene. Using monomer 7 allowed us to use MALDI-TOF to distinguish between Br and I terminators at the end of the P5 chain. The MALDI-TOF analysis confirmed that a high fraction of polymer chains terminated with bithiophene at one end, and with Br rather than with I at the other end (i.e., biTh-(P3OT)-Br). The only potential source of bromine atoms was from the catalytic initiator 4. The conclusion was that "halogen transfer" occurred during sequential monomer addition to the reactive end of the growing polymer chain. The bromine atom was so strongly associated with the reactive end of the chain that it prevailed over the large excess of iodide anion (from Grignard monomer 7). Because the reactive intermediate is a radical, the novel living polymerization can be described formally as an aromatic counterpart to ATRP.

Figure 4:
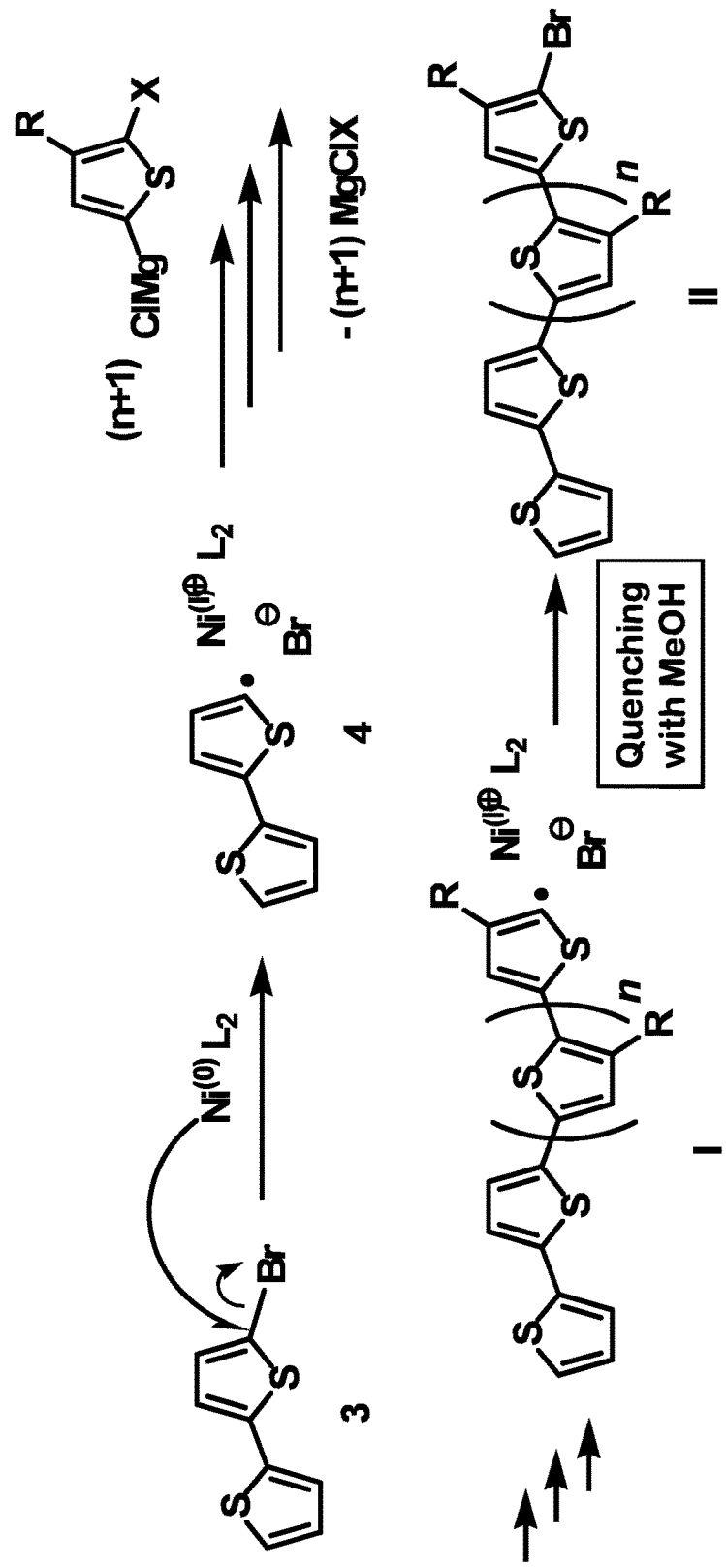
FIG. 4 depicts a proposed mechanism for the novel controlled radical polymerization process.

Based on our initial findings, and without wishing to be bound by this hypothesis, we suggest a mechanistic description of the aromatic ATRP process having a formal resemblance to classical ATRP of alkenes. See FIG. 4. The reaction between 2-bromobithiophene and Ni(dppp)$_2$ likely involves a single-electron transfer from Ni(0) to produce catalytic initiator 4, which has a phosphine ligand-stabilized Ni(I)—Br$^-$ deactivator group closely associated with the radical center on the thiophene. Although the nature of the radical species could not be directly studied by ESR, the radical is likely localized in an sp$^2$ hybrid orbital. (Although we in fact detected a strong signal in the ESR spectrum of catalyst 4, we later found that the activator Ni(dppp)$_2$ showed the same strong signal, perhaps due to the presence of paramagnetic Ni nanoparticle impurities. Thus the ESR measurements were inconclusive on this point.) Analogously to the classic ATRP mechanism, the radical species can remain in a dormant state as a very tight, closely associated group, due to the stabilization of Ni(I) by the phosphine ligands. Addition of Grignard monomer to the dormant radical species initiates a sequence of chain-growth steps, resulting in a longer PT chain that again terminates with a radical center. The absence of $^{31}$P NMR signals supported our conclusion that propagation occurred through radical (paramagnetic) intermediates. When available monomer has been consumed, the reaction stalls as dormant complex I, having an active center similar to that of catalytic initiator 4. Quenching of complex I with methanol destroys the active Ni(I) center, and produces the final Br-terminated PT II. (After this step, we detected free dppp ligand by $^{31}$P NMR.) Other solvents with active hydrogen atoms can also be used to quench the complex through protolysis of the active Ni(I) center, e.g., water, other alcohols, acids, etc. Our proposed mechanism is consistent with all experimentally observed features of the aromatic ATRP process.

Further Examples: Preparation of Catalytic Initiators for Controlled Radical Polymerization of Halogenated Aromatic Grignard Reagents and their Use in Preparation of Conjugated Polymers Example 14

General Procedure for the Preparation of Catalytic Initiator 4

2-Bromobithiophene (0.3 ml of 81.6 mM solution in toluene, 0.025 mmol) was added to a solution of 22 mg (0.025 mmol) of Ni(dppp)$_2$ in 10 ml of toluene at room temperature. The resulting mixture was stirred at 40° C. for 48 h, after which it contained approximately a 2.5 mM concentration of Compound 4. The solution could be stored in a freezer under inert atmosphere for at least 1 month without decreasing its catalytic activity.

Example 15

Representative Procedure for Externally Initiated Controlled Radical Polymerization (Aromatic ATRP): Polymer P1

A solution of i-PrMgCl (0.75 ml of 2.0 M solution in THF, 1.5 mmol) was added dropwise to a stirred solution of 0.49 g (1.5 mmol) of 2,5-dibromo-3-hexylthiophene in 22 ml of THF at 0° C., and the resulting solution was stirred for 1 h at this temperature to yield a solution of Grignard reagent 2. An aliquot of solution of 4 (1.8 ml of 2.5 mM solution in toluene, 4.5 µmol) was added to the Grignard reagent solution at room temperature. The reaction mixture was stirred at 35° C. for 1 h. Precipitation into 120 ml of methanol resulted in a crude, dark-purple polymer which was placed into a Soxhlet extractor, and extracted successively with methanol, hexane, and CHCl$_3$. The chloroform fraction yielded 0.10 g (40%) of polymer P1 as a dark-purple solid, M$_n$ 48 kDa, PDI 1.35 (GPC, vs. polystyrene). $^1$H NMR (400 MHz, CDCl$_3$) δ 6.98 (s, 1H), 2.80 (t, J=7.9 Hz, 2H), 1.78-1.64 (m, 2H), 1.49-1.29 (m, 6H), 0.91 (t, J=6.9 Hz, 3H).

Example 16

Block Copolymer P2

A solution of i-PrMgCl (0.32 ml of 2.0 M solution in THF, 0.64 mmol) was added dropwise to a stirred solution of 0.2 g (0.62 mmol) of 2,5-dibromo-3-hexylthiophene in 15 ml of THF at 0° C., and the resulting solution was stirred for 1 h at this temperature to yield a solution of Grignard reagent 2. An aliquot of a solution of catalytic initiator 4 (2.5 ml of 2.5 mM solution in toluene, 6.2 µmol) was added to the Grignard reagent solution, and the reaction mixture was stirred at 35° C. for 1 h. A solution of the Grignard reagent 5 (prepared separately at 0° C. from 0.25 g (0.62 mmol) of 2-[(2,5-dibromothiophen-3-yl)ethoxy]-tert-butyldimethylsilane in 30 ml of THF and 0.32 ml (0.64 mmol) of 2.0 M solution of i-PrMgCl in THF) was added dropwise over a period of 1 min, and the resulting solution was stirred at 35° C. for additional 1.5 h. Precipitation into 150 ml of methanol resulted in a crude dark-purple polymer which was placed into a Soxhlet extractor, and extracted successively with methanol, hexane, and CHCl$_3$. The chloroform fraction yielded 0.087 g (37%) of block copolymer P2 as a dark-purple solid material, M$_n$ 26 kDa, PDI 1.5 (GPC, vs. polystyrene). $^1$H NMR (400 MHz, CDCl$_3$) δ 7.08 (s, 0.67H), 6.98 (s, 1H), 3.91 (t, J=6.7 Hz, 1.33H), 3.04 (t, J=6.7 Hz, 1.33H), 2.81 (t, J=8.0 Hz, 2H), 1.81-1.63 (m, 2H), 1.49-1.28 (m, 6H), 0.90 (s, 6H), 0.05 (s, 4H). Based on the $^1$H NMR data, the ratio of P3HT to poly[3-(TBDMSO-ethyl)thiophene] blocks was ~1.5:1.

Example 17

Block Copolymer P3

A solution of i-PrMgCl (0.32 ml of 2.0 M solution in THF, 0.64 mmol) was added dropwise to a stirred solution of 0.25 g (0.62 mmol) of 2-[(2,5-dibromothiophen-3-yl)ethoxy]-tert-butyldimethylsilane in 25 ml of THF at 0° C., and the resulting solution was stirred for 1 h at this temperature to yield a solution of Grignard reagent 5. An aliquot of initiator solution 4 (2.5 ml of 2.5 mM solution in toluene, 6.2 µmol) was added to the Grignard reagent solution, and the reaction mixture was stirred at 35° C. for 1 h. A solution of Grignard reagent 2 (prepared separately at 0° C. from 0.2 g (0.62 mmol) of 2,5-dibromo-3-hexylthiophene in 22 ml of THF and 0.32 ml (0.64 mmol) of 2.0 M solution of i-PrMgCl in THF) was added dropwise over a period of 1 min, and the resulting solution was stirred at 35° C. for additional 1.5 h. Precipitation into 150 ml of methanol resulted in a crude, dark-purple polymer which was placed into a Soxhlet extractor, and extracted successively with methanol, hexane, and CHCl$_3$. The chloroform fraction yielded 0.073 g (30%) of block copolymer P3 as a dark-purple solid material, $M_n$ 48 kDa, PDI 1.4 (GPC, vs. polystyrene). $^1$H NMR (400 MHz, CDCl$_3$) δ 7.08 (s, 0.67H), 6.98 (s, 1H), 3.91 (t, J=6.7 Hz, 1.33H), 3.04 (t, J=6.8 Hz, 1.33H), 2.81 (t, J=8.0 Hz, 2H), 1.81-1.63 (m, 2H), 1.49-1.28 (m, 6H), 0.90 (s, 6H), 0.05 (s, 4H). Based on $^1$H NMR, the ratio of P3HT to poly[3-(TBDMSO-ethyl)thiophene] blocks was ~1.5:1.

Example 18

Polymer P4 was prepared following the representative procedure for polymer P1, starting from 0.25 g (0.7 mmol) of 2,5-dibromo-3-octylthiophene in 11 ml of THF, 0.35 ml of 2.0 M solution of i-PrMgCl in THF (0.7 mmol), and using 0.85 ml of 2.5 mM solution of the catalytic initiator 4 in toluene (2.1 µmol). Purification of the crude polymer using Soxhlet extraction yielded 0.04 g (30%) of P4 as a dark-purple solid material, $M_n$ 57 kDa, PDI 1.5 (GPC, vs. polystyrene). $^1$H NMR (250 MHz, CDCl$_3$) δ 6.97 (s, 1H), 2.80 (t, J=7.8 Hz, 2H), 1.84-1.59 (m, 2H), 1.56-1.05 (m, 10H), 1.01-0.75 (m, 3H).

Example 19

Polymer P5 was prepared following the representative procedure given above for polymer P1, starting from 0.2 g (0.45 mmol) of 2,5-diiodo-3-octylthiophene in 11 ml of THF, 0.22 ml of 2.0 M solution of i-PrMgCl in THF (0.45 mmol), and using 0.53 ml of 2.5 mM solution of the catalytic initiator 4 in toluene (1.33 µmol). Purification of the crude polymer using Soxhlet extraction yielded 0.016 g (19%) of polymer P5 as a dark-purple, solid material, $M_n$ 9 kDa, PDI 1.5 (GPC, vs. polystyrene). $^1$H NMR (250 MHz, CDCl$_3$) δ 6.97 (s, 1H), 2.80 (t, J=7.8 Hz, 2H), 1.84-1.59 (m, 2H), 1.56-1.05 (m, 10H), 1.01-0.75 (m, 3H).

Figure 5:
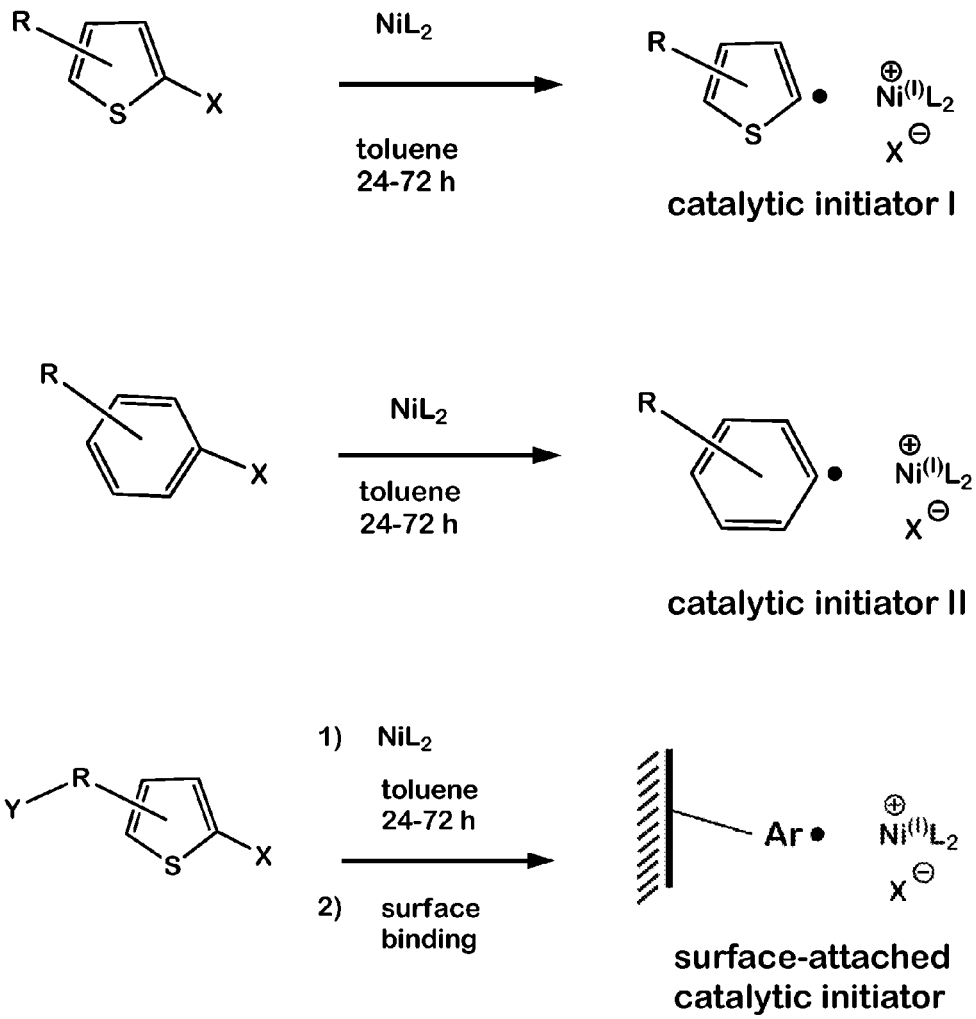
FIGS. 5, 6, 7, 8, 9, 10, and 11 depict the preparation of catalytic initiators in accordance with this invention, and their use in controlled radical polymerizations, including their use as surface-bound catalytic initiators to prepare surface-bound conjugated polymer films.

Catalytic initiators were prepared by reacting an aryl halide with excess NiL$_2$ (the Ni(0) complex with two bidentate biphosphine ligands) at slightly elevated temperature in toluene (or other suitable solvent) for 24-72 h. See FIG. 5.

The catalytic initiators can be stored under refrigeration in solution for at least one month. They can be used as external catalytic initiators in the preparation of various conjugated polymers and block copolymers through controlled radical polymerization of Grignard monomers or functionalized Grignard monomers. The polymerization involves adding catalytic initiator solution (from about 0.01 mol-% to about 1 mol-% (or higher) active catalyst, depending on the desired molecular weight of the polymer) to a solution of the Grignard monomer, and allowing the components to react at about 25° C. to about 35° C. with stirring (typically for about 1 hour). If a block copolymer is desired, then a second Grignard monomer can be added after a time, allowed to react for an additional period, and so forth. Following polymerization, the crude polymer is precipitated into methanol, and is purified (e.g. by Soxhlet extraction).

Figure 6:
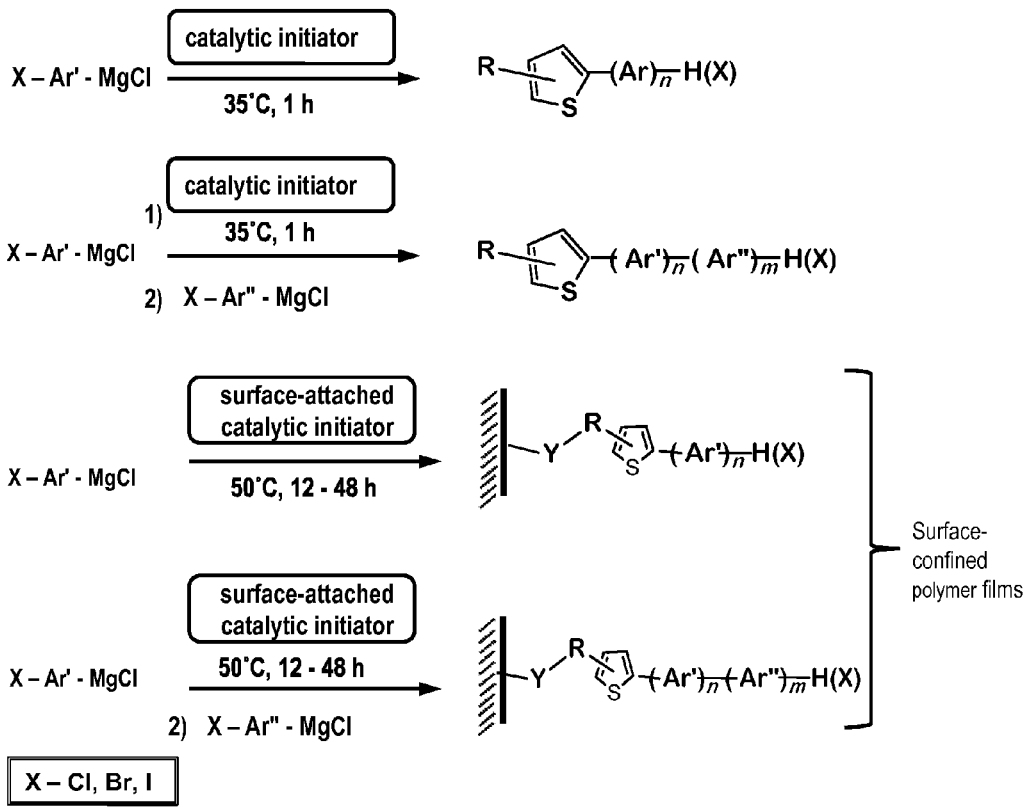
Figure 6:
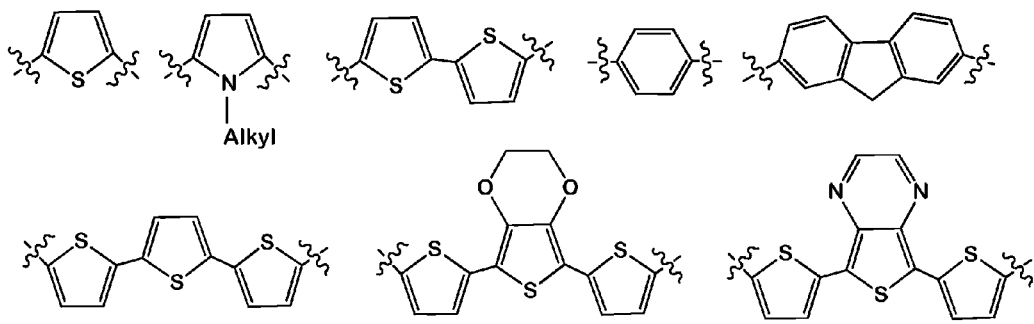
Figure 7:
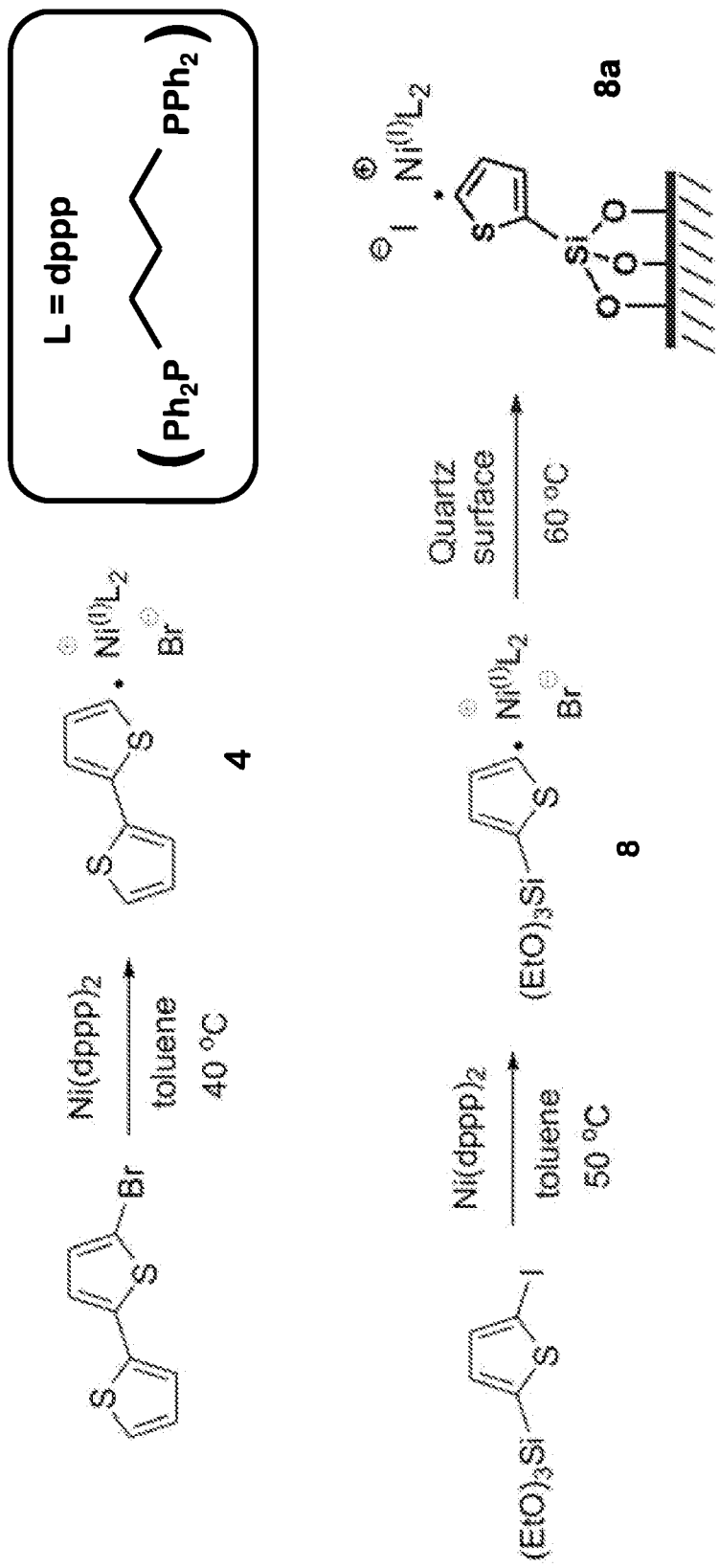
Figure 8:
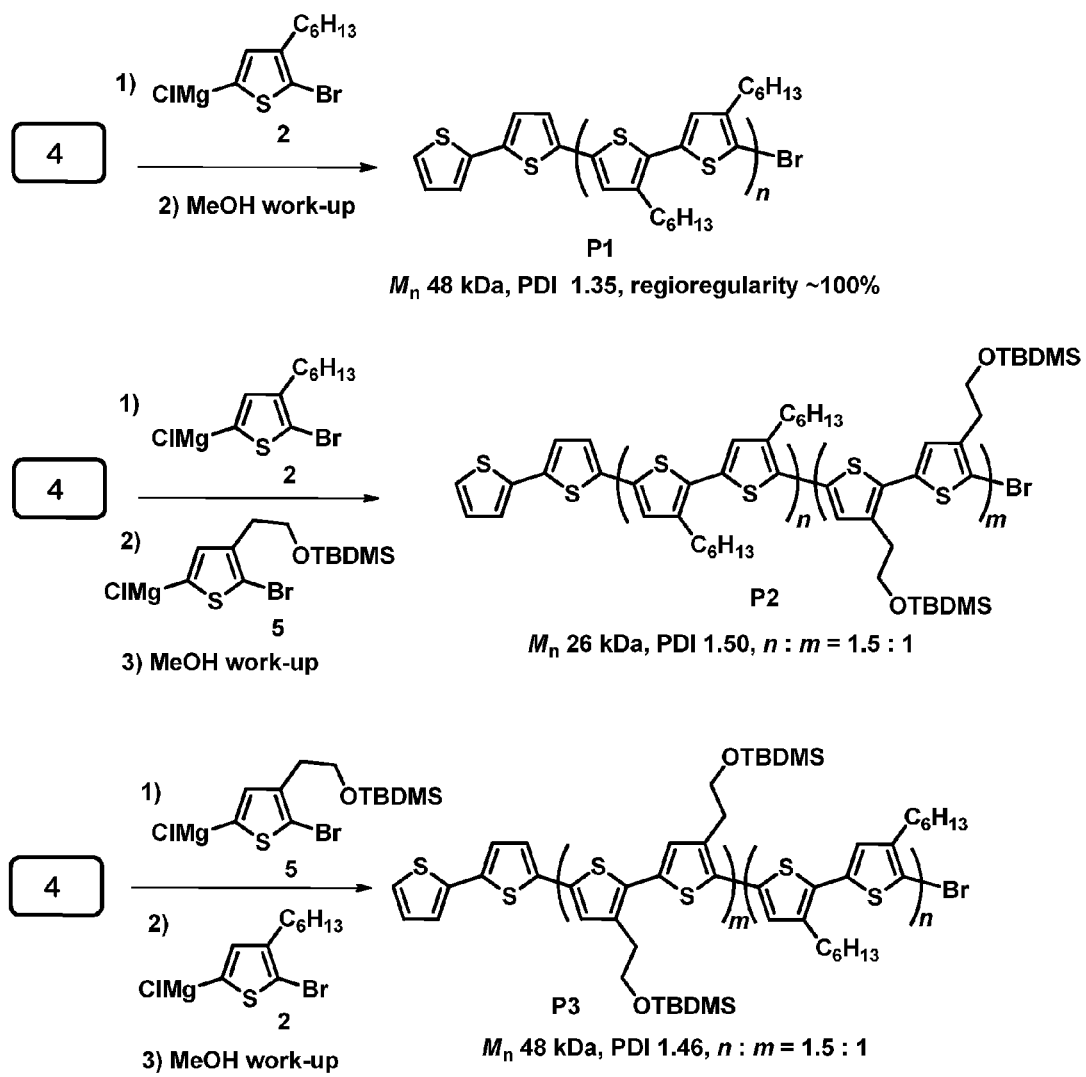
Figure 9:
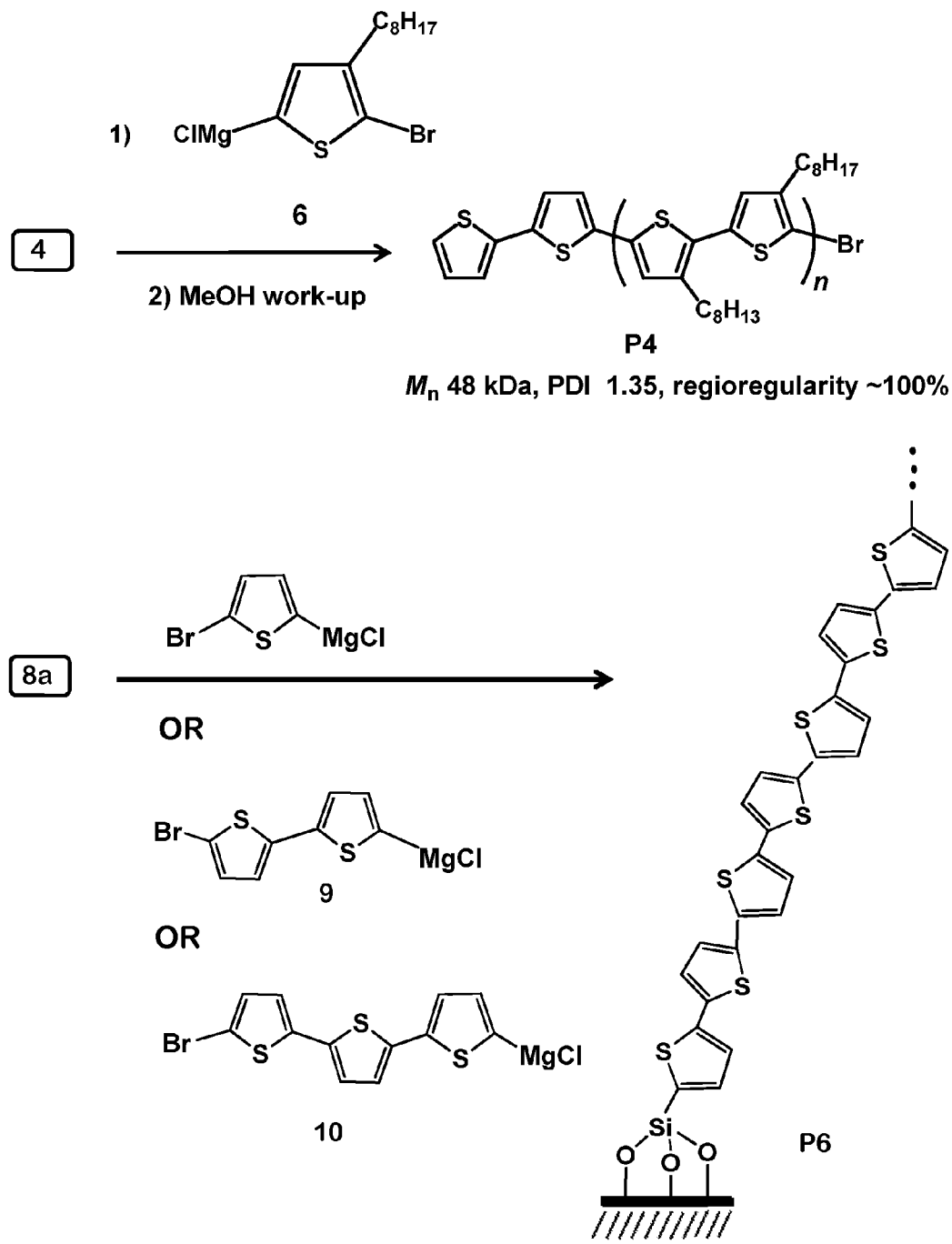
Figure 10:
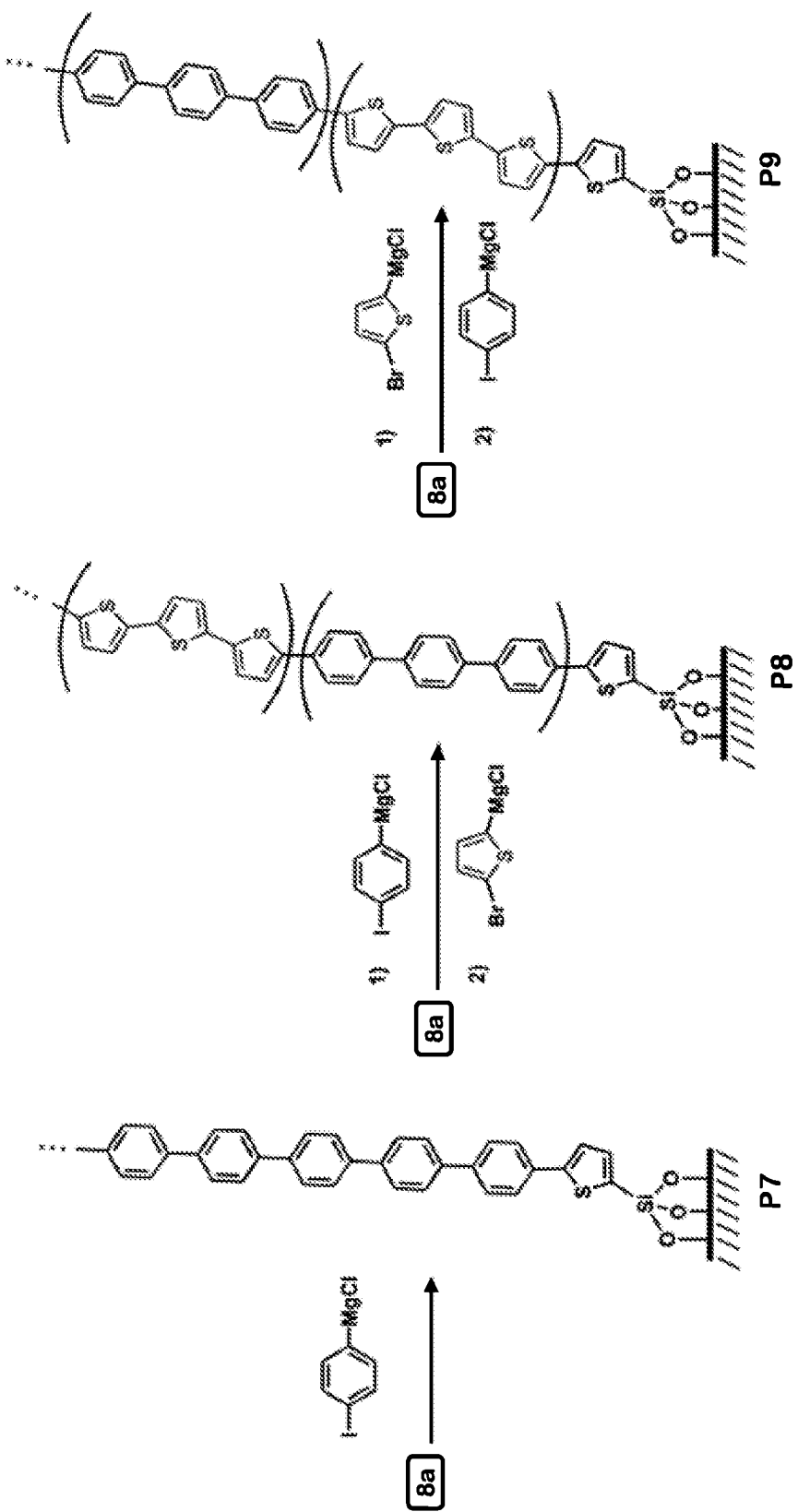
Figure 11:
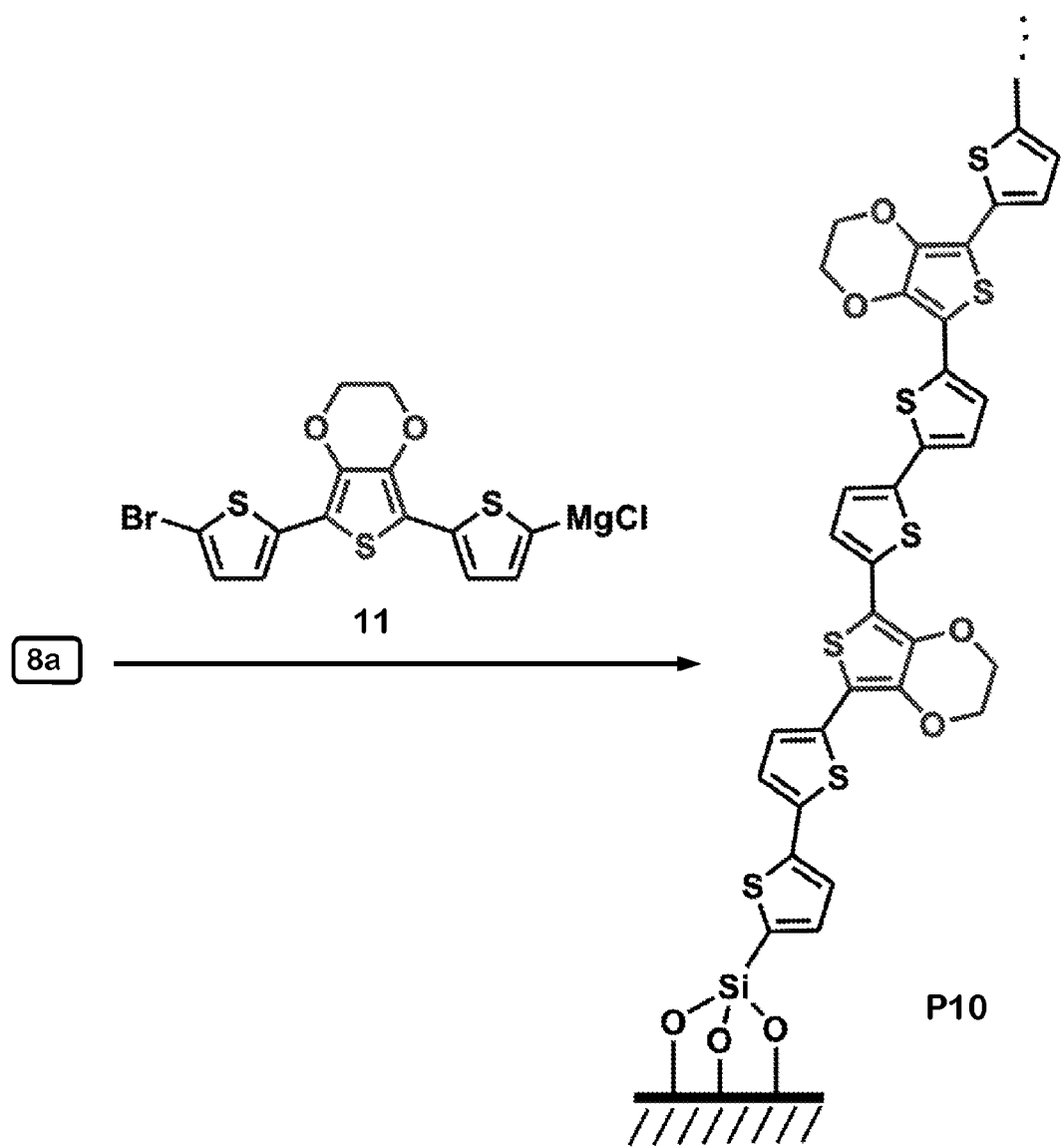

Alternatively, if an R group in catalytic initiator I or II includes an anchoring group for chemical attachment to a surface (e.g., to a surface of silica, glass, metal oxide, polymer, etc.), then the anchor can be used to initiate surface-confined polymerization to produce a surface-attached, conjugated polymer film or brush. Such films can be used, for example, in electronic applications. See, e.g., FIGS. 5 and 6. In many cases, structures made with polymers in accordance with the present invention cannot be made by more traditional methods, such as melting, extrusion, solution spin-casting, or ink-jet printing. They may, however, be directly "cast" from solution via surface polymerization in accordance with the present invention.

FIGS. 7, 8, 9, 10, and 11 depict examples of catalytic initiators, e.g., compounds 4 and 8, and their use in the preparation of regioregular polymers—e.g., poly(3-hexylthiophene) P1, poly(3-octylthiophene) P4; block copolymers—e.g., P2 and P3; surface-attached films of polymers—e.g., polythiophene P6, poly(p-phenylene) P7; surface-attached films of block copolymers—e.g., P8 and P9; and surface-attached films of copolymers—e.g., P10.

An optional feature of the novel controlled radical polymerization method is that it permits the polymerization of "oligomeric" monomers (i.e., monomers that contain more than one aromatic unit). This option is especially useful for surface-confined polymerization, which is intrinsically more difficult due to the heterogeneous nature of most surfaces; and it is also useful for the preparation of copolymers. Examples of such preparations are thin films of polythiophene P6, prepared from monomers 9 and 10, and thin films of copolymer P10 prepared, from monomer 11.

Example 20

Polymerization Initiator 8

A mixture of 44 mg (0.05 mmol) of Ni(dppp)$_2$ and 9.0 mg (0.025 mmol) of 2-triethoxysilyl-5-iodothiophene in 10 ml of toluene was stirred at 40° C. for 12 h, and the resulting solution (in which the nominal concentration of compound 8 was 2.5 mM) was used for surface immobilization without further purification.

Example 21

Activation of Quartz Substrates

Rectangular quartz slides (approx. 1.1×2.5 cm$^2$) were ultrasonicated sequentially for 10 minutes each in CHCl$_3$, methanol, and deionized water. These ultrasonicated slides were then placed into a Piranha solution (a mixture of conc. H$_2$SO$_4$ and 30% H$_2$O$_2$ (7:3)) and ultrasonicated for an additional 30 min. After rinsing with copious amounts of deionized water, the quartz substrates were dried in N$_2$ flow at room temperature for 4 h, and then activated using O$_2$ plasma for 10 min.

Example 22

Preparation of Surface-Immobilized Initiator 8a

Activated quartz slides were immersed into a solution of polymerization catalytic initiator 8 in toluene and kept at 60° C. for 3 days followed by gentle rinsing with anhydrous toluene. Due to the air-sensitive nature of the compounds involved, all procedures were carried out inside a glove box.

Example 23

Representative Procedure for Preparation of Conjugated Polymer Films by Surface-Initiated Polymerization Using Initiator 8: Preparation of Polythiophene P6 Thin Films Quartz substrates were first modified with an initiator 8a monolayer, and then were immersed in a 0.1 M solution of Grignard monomer ((5-bromothien-2-yl)magnesium chloride) in THF (prepared from 0.24 g (1.0 mmol) of 2,5-dibromothiophene in 10 ml of THF and 0.5 ml of 2.0 M solution of i-PrMgCl (1.0 mmol)). The reaction mixture was gently stirred for 16 hours at 40° C., and the substrates were rinsed with anhydrous toluene. Then the PT-covered substrates were immersed in a 5 mM solution of Ni(dppp)$_2$ in toluene for 1 day. After residual Ni(dppp)$_2$ was removed by washing with anhydrous toluene three times, the regenerated thin films were again immersed in a 0.1 M solution of Grignard monomer in THF with gentle stirring for 16 h at 40° C. At the end of the reaction period, the reactive Ni(I) centers were quenched by placing the substrates into methanol and ultrasonicating for 10 min. The resulting PT thin films were further cleaned by ultrasonication in CHCl$_3$ (2×10 min).

Example 24

Preparation of a Thin Film of Block Copolymer P8

Quartz substrates were first modified with initiator 8a monolayer and then immersed in a 0.03 M solution of 4-iodophenylmagnesium chloride (prepared from 0.10 g (0.3 mmol) of 1,4-diiodobenzene and 0.15 ml of 2.0 M solution of i-PrMgCl (0.3 mmol) at 0° C.) at 25° C. for 12 h with gentle stirring. Then the substrate was rinsed with toluene and immersed in a 5 mM solution of Ni(dppp)$_2$ for 8 h. After residual Ni(dppp)$_2$ was removed by washing with toluene, the substrate was placed in a 0.05 M solution of (5-bromothien-2-yl)magnesium chloride (prepared from 0.12 g (0.5 mmol) of 2,5-dibromothiophene in 10 ml of THF and 0.25 ml of 2.0 M solution of i-PrMgCl (0.5 mmol) at 0° C.) at 25° C. for 8 h with gentle stirring. At the end of the polymerization, the substrate was placed in methanol and ultrasonicated for 10 min, followed by ultrasonication in CHCl$_3$ (2×10 min).

Example 25

Preparation of a Thin Film of Copolymer P10

This polymerization was carried out following the representative procedure described above for thin films of polymer P6, using Grignard monomer 11, which had been prepared by reacting equimolar amounts of 2,5-bis(5-bromothien-2-yl)-3,4-dioxythiophene and i-PrMgCl. The polymerization was carried out at 45° C. for 12 h.

Example 26

Characterization of the Thin Films

Figures 12A, 12B, 12C:
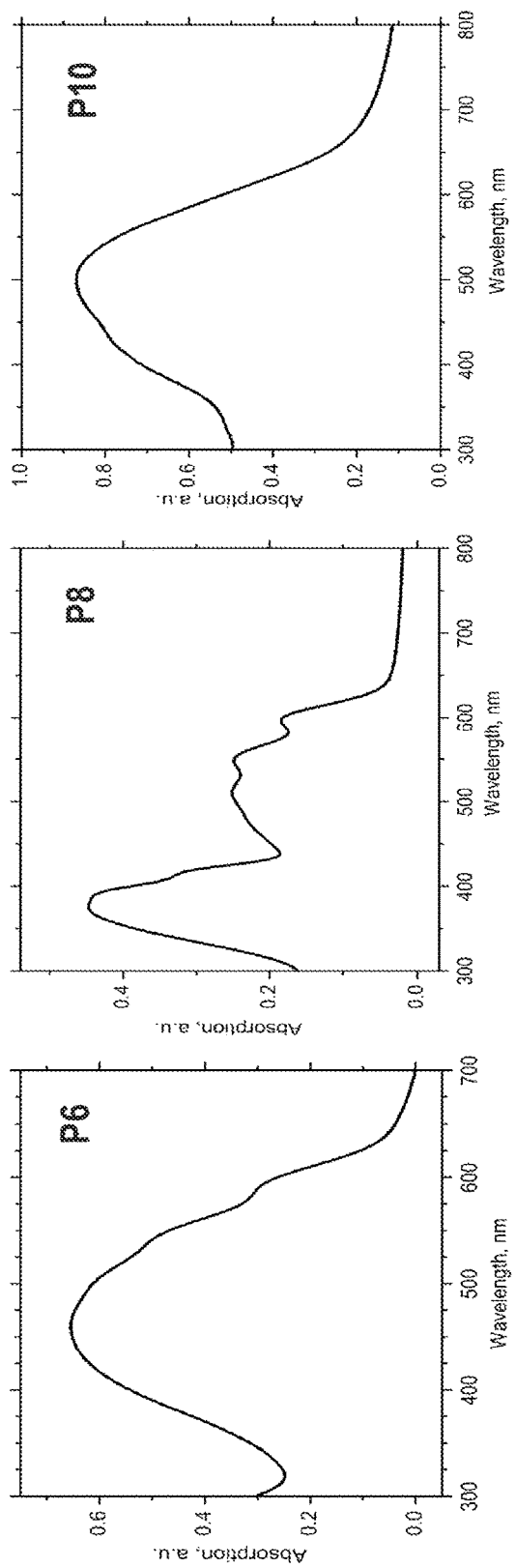
FIG. 12 depicts UV/Vis absorption spectra for three conjugated polymer films prepared by controlled radical polymerization.

The thin films of conjugated polymers and copolymers were characterized by UV/Vis absorption spectroscopy and Atomic Force Microscopy (AFM). The results indicated that the films had high density and a uniform surface morphology. The representative UV/vis absorption spectra for polymers P6, P8 and P10 (prepared as described above, P6 prepared from (5-bromothien-2-yl)magnesium chloride monomer) are shown in FIG. 12. The UV/Vis spectra confirmed that dense and thick films of the polymers had been prepared. The AFM images (not shown) confirmed that the surface had been uniformly covered by polymer.

The complete disclosures of all references cited in this specification are hereby incorporated by reference, including the complete disclosure of the 61/503,727 priority application. Also incorporated by reference are the complete disclosures of the following abstracts and presentations by the inventors and their colleagues: (1) Hwang, E.; Choi, J.; Lusker, K. L.; Garno, J. C.; Nesterov, E. E. "Nanopatterned polythiophene thin films prepared by surface-initiated polymerization." International Chemical Congress of Pacific Basin Societies (Pacifichem 2010), Honolulu, Hi., 2010. Abstr. 33 (Dec. 15-20, 2010; Abstract published Jul. 12, 2010); (2) Choi, J.; Nesterov, E. E. "Highly efficient externally initiated Kumada polycondensation: controlled preparation of complex polythiophene architectures." International Chemical Congress of Pacific Basin Societies (Pacifichem 2010), Honolulu, Hi., 2010. Abstr. 1192 (Dec. 15-20, 2010; Abstract published Jul. 12, 2010); (3) Choi, J.; Daniels, S. L.; Garno, J. C. Nesterov, E. E. "Supramolecular organization in stimuli-responsive amphiphilic conjugated polythiophene block copolymers." 66th Southwest and 62nd Southeast ACS Regional Meeting, New Orleans, La., 2010. Abstr. SESW-1017 (Nov. 30-Dec. 4, 2010; Abstract published approximately November 2010); (4) Hwang, E.; Choi, J.; Lusker, K. L.; Garno, J. C.; Nesterov, E. E. "Nanopatterned surface-immobilized polythiophene thin films by surface initiated metal-catalyzed living polymerization." 66th Southwest and 62nd Southeast ACS Regional Meeting, New Orleans, La., 2010. Abstr. SESW-478 (Nov. 30-Dec. 4, 2010; Abstract published approximately November 2010); (5) Lusker, K. L.; Hwang, E.; Nesterov, E. E.; Garno, J. C. "Nanopatterns as selective sites for surface chemical reactions." 66th Southwest and 62nd Southeast ACS Regional Meeting, New Orleans, La., 2010. Abstr. SESW-375 (Nov. 30-Dec. 4, 2010; Abstract published approximately November 2010); (6) Choi, J.; Nesterov, E. E. "Preparation of polythiophene block-copolymers incorporating low energy gap group using nickel catalyzed quasi-living polymerization." 239th ACS National Meeting, San Francisco, Calif., 2010. Abstr. POLY-284 (Mar. 21-25, 2010; Abstract published approximately February-March 2010); (7) Jinwoo Choi "Semiconducting Polymers and Block Copolymers Prepared by Chain-Growth Living Polymerization" (PhD dissertation, Louisiana State University, Baton Rouge, La., August 2011); and (8) Euiyong Hwang "Surface-Initiated Polymerization as a Novel Strategy towards Preparation of Organic Semiconducting Polymer Thin Films" (PhD Dissertation, Louisiana State University, Baton Rouge, La. May 2011). Where applicable, these incorporations by reference include any supplemental material associated with a particular publication. In the event of an otherwise irreconcilable conflict, however, the present specification shall control. E.g., there are certain portions of the present specification that supersede certain portions of the provisional priority disclosure.

What is claimed:

1. A method of synthesizing a catalyst, said method comprising reacting in solution Ar—X with $NiL_2$ wherein:
   Ar denotes bithiophen-2-yl;
   each of the two L ligands is 1,3-bis(diphenylphosphino) propane; and
   X denotes bromine.

2. The method of claim 1, additionally comprising the step of storing the catalyst in solution.

3. The method of claim 2, wherein the catalyst is stored in solution under refrigeration.

4. The method of claim 3, wherein the catalyst is stored in solution under refrigeration for at least one month.

* * * * *